(12) United States Patent
Layne et al.

(10) Patent No.: US 6,770,087 B2
(45) Date of Patent: Aug. 3, 2004

(54) PARTIAL ENCAPSULATION OF STENTS

(75) Inventors: Richard Layne, Phoenix, AZ (US); Sandra Cundy, Mesa, AZ (US); Debra Bebb, Mesa, AZ (US)

(73) Assignee: Bard Peripheral Vascular, Inc., Tempe, AZ (US)

(*) Notice: Subject to any disclaimer, the term of this patent is extended or adjusted under 35 U.S.C. 154(b) by 0 days.

(21) Appl. No.: 09/848,740

(22) Filed: May 3, 2001

(65) Prior Publication Data

US 2001/0032009 A1 Oct. 18, 2001

Related U.S. Application Data

(62) Division of application No. 09/388,496, filed on Sep. 2, 1999, now Pat. No. 6,398,803.
(60) Provisional application No. 60/118,269, filed on Feb. 2, 1999.

(51) Int. Cl.[7] ................................................. A61F 2/06
(52) U.S. Cl. ....................................... 623/1.13; 623/901
(58) Field of Search ............................. 623/1.13, 1.27, 623/1.44, 1.49, 901, 921; 604/526, 264; 264/510, 512

(56) References Cited

U.S. PATENT DOCUMENTS

| 4,324,574 | A | | 4/1982 | Fagan |
| 4,647,416 | A | * | 3/1987 | Seiler et al. ................. 264/118 |
| 4,776,337 | A | | 10/1988 | Palmaz |
| 4,954,126 | A | | 9/1990 | Wallsten |
| 5,078,736 | A | | 1/1992 | Behl |
| 5,122,154 | A | | 6/1992 | Rhodes |
| 5,123,917 | A | | 6/1992 | Lee |
| 5,139,480 | A | | 8/1992 | Hickle et al. |
| 5,158,548 | A | | 10/1992 | Lau et al. |
| 5,211,658 | A | | 5/1993 | Clouse |
| 5,234,456 | A | * | 8/1993 | Silvestrini ..................... 623/1.2 |
| 5,236,447 | A | | 8/1993 | Kubo et al. |
| 5,242,399 | A | | 9/1993 | Lau et al. |
| 5,258,027 | A | | 11/1993 | Berghaus |
| 5,282,823 | A | | 2/1994 | Schwartz et al. |
| 5,344,426 | A | | 9/1994 | Lau et al. |
| 5,354,309 | A | | 10/1994 | Schnepp-Pesch et al. |

(List continued on next page.)

FOREIGN PATENT DOCUMENTS

| EP | 0 603 959 A1 | 6/1994 |
| EP | 792 627 | 9/1997 |
| EP | 893 108 | 1/1999 |
| FR | 2 671 482 A1 | 7/1992 |
| WO | WO 94/24961 | 11/1994 |
| WO | WO 96/28115 | 9/1996 |
| WO | WO 97/21403 | 6/1997 |
| WO | WO 98/26731 | 6/1998 |
| WO | WO 98/38947 | 9/1998 |

Primary Examiner—Brian E Pellegrino
(74) Attorney, Agent, or Firm—Morrison & Foerster, LLP

(57) ABSTRACT

Partially encapsulated stents are made using gaps cut into ePTFE covering material. Ring stents are placed over an inner ePTFE tube (e.g., supported on a mandrel) and are covered by a "lacey" graft sleeve, which is constructed by cutting apertures into an ePTFE tube so that a series of circumferential and longitudinal strips is created. This "lacey" sleeve is then laminated to the inner ePTFE tube to capture the stents. By selecting the size and position of the apertures in the ePTFE covering, it is possible to leave critical parts of the stent unencapsulated to facilitate flexibility and expansion. Alternatively, the gaps can consist of slits cut into the ePTFE covering material. These slits can be cut in any direction including longitudinally, radially, or diagonally. In addition, the slits can be spaced at varying intervals around the covering material to maximize flexibility and expandability. Although a single stent can be used, these approaches lend themselves to use of a plurality of individual ring stents spaced apart along the inner ePTFE tube.

8 Claims, 3 Drawing Sheets

U.S. PATENT DOCUMENTS

| | | | |
|---|---|---|---|
| 5,383,928 | A | 1/1995 | Scott et al. |
| 5,384,019 | A | 1/1995 | Keating et al. |
| 5,389,106 | A | 2/1995 | Tower |
| 5,395,390 | A | 3/1995 | Simon et al. |
| 5,421,955 | A | 6/1995 | Lau et al. |
| 5,437,083 | A | 8/1995 | Williams et al. |
| 5,443,496 | A | 8/1995 | Schwartz et al. |
| 5,458,615 | A | 10/1995 | Klemm et al. |
| 5,474,563 | A | 12/1995 | Myler et al. |
| 5,507,767 | A | 4/1996 | Maeda et al. |
| 5,507,768 | A | 4/1996 | Lau et al. |
| 5,514,154 | A | 5/1996 | Lau et al. |
| 5,522,881 | A | 6/1996 | Lentz |
| 5,527,353 | A | 6/1996 | Schmitt |
| 5,527,355 | A | 6/1996 | Ahn |
| 5,546,646 | A | 8/1996 | Williams et al. |
| 5,549,663 | A | 8/1996 | Cottone, Jr. |
| 5,554,181 | A | 9/1996 | Das |
| 5,569,295 | A | 10/1996 | Lam |
| 5,573,520 | A * | 11/1996 | Schwartz et al. ............ 604/264 |
| 5,591,223 | A | 1/1997 | Lock et al. |
| 5,593,417 | A | 1/1997 | Rhodes |
| 5,603,721 | A | 2/1997 | Lau et al. |
| 5,632,840 | A | 5/1997 | Campbell |
| 5,645,559 | A | 7/1997 | Hachtman et al. |
| 5,649,950 | A | 7/1997 | Bourne et al. |
| 5,649,977 | A | 7/1997 | Campbell |
| 5,653,727 | A | 8/1997 | Wiktor |
| 5,653,747 | A | 8/1997 | Dereume |
| 5,667,523 | A | 9/1997 | Bynon et al. |
| 5,683,453 | A | 11/1997 | Palmaz |
| 5,693,085 | A | 12/1997 | Buirge et al. |
| 5,700,286 | A | 12/1997 | Taraglia et al. |
| 5,713,949 | A | 2/1998 | Jayaraman |
| 5,718,973 | A | 2/1998 | Lewis et al. |
| 5,723,003 | A | 3/1998 | Winston et al. |
| 5,728,131 | A | 3/1998 | Frantzen et al. |
| 5,728,158 | A | 3/1998 | Lau et al. |
| 5,735,892 | A | 4/1998 | Myers et al. |
| 5,735,893 | A | 4/1998 | Lau et al. |
| 5,738,674 | A | 4/1998 | Williams et al. |
| 5,749,880 | A | 5/1998 | Banas et al. |
| 5,755,770 | A | 5/1998 | Ravenscroft |
| 5,755,774 | A | 5/1998 | Pinchuk |
| 5,766,238 | A | 6/1998 | Lau et al. |
| 5,769,884 | A | 6/1998 | Solovay |
| 5,810,870 | A | 9/1998 | Myers et al. |
| 5,824,037 | A | 10/1998 | Fogarty et al. |
| 5,824,043 | A | 10/1998 | Cottone, Jr. |
| 5,824,046 | A | 10/1998 | Smith et al. |
| 5,824,054 | A | 10/1998 | Khosravi et al. |
| 5,843,161 | A | 12/1998 | Solovay |
| 5,843,166 | A | 12/1998 | Lentz et al. |
| 5,849,037 | A | 12/1998 | Frid |
| 5,851,232 | A | 12/1998 | Lois |
| 5,876,448 | A | 3/1999 | Thompson et al. |
| 5,928,279 | A | 7/1999 | Shannon et al. |
| 6,004,348 | A | 12/1999 | Banas et al. |
| 6,015,431 | A | 1/2000 | Thornton et al. |
| 6,042,605 | A | 3/2000 | Martin et al. |

* cited by examiner

PARTIAL ENCAPSULATION OF STENTS

This application is a division of US. application Ser. No. 09/388,496, filed Sep. 2, 1999, now U.S. Pat. No. 6,398,803, which claims the benefit of U.S. Provisional Application No. 60/118,269, filed Feb. 2, 1999, each of which are hereby incorporated by reference.

BACKGROUND OF THE INVENTION

1. Field of the Invention

The present invention relates generally to the field of medical devices, and more particularly, to encapsulation of stents.

2. Description of Related Art

Stents and related endoluminal devices are currently used by medical practitioners to treat portions of the vascular system that become so narrowed that blood flow is restricted. Stents are tubular structures, usually of metal, which are radially expandable to hold a narrowed blood vessel in an open configuration. Such narrowing (stenosis) occurs, for example, as a result of the disease process known as arteriosclerosis. Angioplasty of a coronary artery to correct arteriosclerosis may stimulate excess tissue proliferation which then blocks (restenosis) the newly reopened vessel. While stents are most often used to "prop open" blood vessels, they can also be used to reinforce collapsed or narrowed tubular structures in the respiratory system, the reproductive system, biliary ducts or any other tubular body structure. However, stents are generally mesh-like so that endothelial and other cells can grow through the openings resulting in restenosis of the vessel.

Polytetrafluoroethylene (PTFE) has proven unusually advantageous as a material from which to fabricate blood vessel grafts or prostheses used to replace damaged or diseased vessels. This is partially because PTFE is extremely biocompatible causing little or no immunogenic reaction when placed within the human body. This is also because in its preferred form, expanded PTFE (ePTFE), the material is light and porous and is potentially colonized by living cells becoming a permanent part of the body. The process of making ePTFE of vascular graft grade is well known to one of ordinary skill in the art. Suffice it to say that the critical step in this process is the expansion of PTFE into ePTFE following extrusion from a paste of crystalline PTFE particles. Expansion represents a controlled longitudinal stretching in which the PTFE is stretched up to several hundred percent of its original length. During the expansion process fibrils of PTFE are drawn out of aggregated PTFE particle (nodes), thereby creating a porous structure.

If stents could be enclosed in ePTFE, cellular infiltration could be limited, hopefully preventing or limiting restenosis. Early attempts to produce a stent enshrouded with ePTFE focused around use of adhesives or physical attachment such as suturing. However, such methods are far from ideal, and suturing, in particular, is very labor intensive. More recently, methods have been developed for encapsulating a stent between two tubular ePTFE members whereby the ePTFE of one-member contacts and bonds to the ePTFE of the other member through the openings in the stent. However, such a monolithically encapsulated stent tends to be rather inflexible. In particular, radial expansion of the stent may stress and tear the ePTFE. There is a continuing need for a stent that is encapsulated to prevent cellular intrusion and to provide a smooth inner surface blood flow and yet still capable of expansion without tearing or delaminating and is relatively more flexible.

SUMMARY OF THE INVENTION

The present invention is directed to encapsulated stents wherein flexibility of the stent is retained, despite encapsulation.

It is an object of this invention to provide a stent device that has improved flexibility, yet maintains its shape upon expansion.

It is also an object of this invention to provide a stent encapsulated to prevent cellular infiltration wherein portions of the stent can move during radial expansion without stressing or tearing the encapsulating material.

These and additional objects are accomplished by an encapsulation process that leaves portions of the stent free to move during expansion without damaging the ePTFE covering. The most basic form of this invention is produced by placing a stent over an inner ePTFE member (e.g., supported on a mandrel) and then covering the outer surface of the stent with an outer ePTFE tube into which slits have been cut. The outer ePTFE tube is then laminated to the inner ePTFE through openings in the stent structure to capture the stent. By selecting the size and location of the slits it is possible to leave critical parts of the stent unencapsulated to facilitate flexibility and expansion. Not only does the slit prevent capture of the underlying PTFE, it forms a focal point for the PTFE to flex. A more complex form of the process is to place over the stent an ePTFE sleeve into which apertures have been cut. This "lacey" outer sleeve leaves portions of the stent exposed for increased flexibility and for movement of the stent portions during expansion without damaging the ePTFE. Although a single stent can be used, these approaches lend themselves to use of a plurality of individual ring stents spaced apart along an inner ePTFE tube and covered by a "lacey" ePTFE sleeve.

In the present invention, individual ring stents are partially encapsulated using the procedure outlined above. Preferably, ring stents of zigzag sinusoidal structure are placed "in phase" (e.g., peaks and valleys of one stent aligned with those of a neighboring stent) on the surface of a tubular ePTFE graft supported by a mandrel. A sleeve of ePTFE is cut using $CO_2$ laser so that openings are created, resulting in a "lacey" pattern. This "lacey" sleeve is then placed over the ring stents. The resulting structure is then subjected to heat and pressure so that regions of ePTFE become laminated or fused together where the lacey sleeve contacts the tubular graft. In addition, the ends of the stent can be completely encapsulated, by known methods, to stabilize the overall structure.

A more complete understanding of the encapsulation process will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

The present invention satisfies the need for an encapsulated stent device to prevent restenosis that is flexible upon expansion and contraction so that the general structural form is retained. This is accomplished encapsulating a stent or a plurality of stent rings using an ePTFE covering into which openings have been cut.

Figure 1:
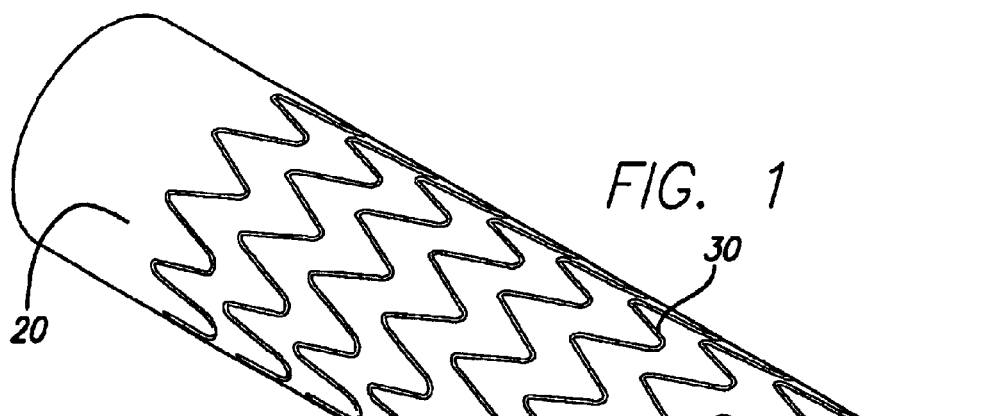
FIG. 1 is a perspective view of a tubular ePTFE member with individual ring stents arranged thereon.
Figure 3:
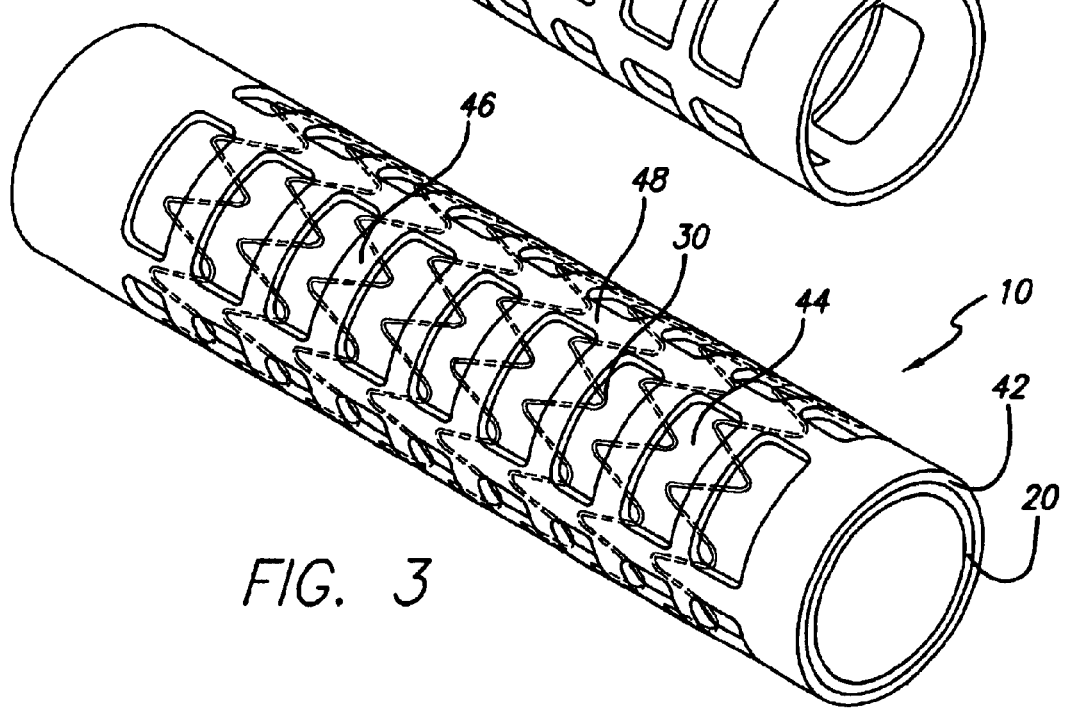
FIG. 3 is a perspective view of the sleeve in FIG. 2 placed over the structure of FIG. 1.

Referring now to the drawings, in which like reference numbers represent similar or identical structures throughout, FIG. 1 illustrates an initial step in constructing the partially encapsulated stent of the present invention. A tubular ePTFE graft 20 is placed over a mandrel for the assembly of a device 10 (FIG. 3). A stent is then placed over the graft 20. In a preferred embodiment, as shown in FIG. 1, a series of zigzag sinusoidal ring stents 30 are placed over the outer surface of the graft 20. Alternatively, one or more stents wherein each stent comprises more than one ring or hoop (e.g., where the rings are helically connected) can be used. The ring stents 30 can be made of any material but a preferred material is metal. The zigzag ring stents 30 may be assembled "in phase" with each adjacent ring stent having peaks and valleys aligned. Alternatively, the individual stents 30 can be "out of phase" to different degrees. It will be apparent that the phase relation of adjacent stents 30 will alter the lateral flexibility as well as the longitudinal compressibility of the structure. The phase relationship can be varied along the length of the device 10, thereby altering the physical properties in different portions of the device 10. Having individual ring stents 30, as opposed to a single tubular stent, provides the advantage that the periodicity, or the number and precise shape of the zigzags per ring, can readily be varied along the length of the graft to influence flexibility and stability properties of the structure. Also, spacing of the individual stents (number of stents per unit length) as well as the phase relationship of stent to stent can be varied to produce stent grafts with desired properties. By placing the ring stents 30 over the outer surface of the tubular ePTFE graft 20, the resulting structure has an inner (luminal) surface that is completely smooth to facilitate the flow of blood. However, there may be instances where the ring stents 30 or other tubular stents are advantageously placed in contact with the inner graft surface or on both the inner and outer surfaces, as one of ordinary skill in the art will readily appreciate.

Figure 2:
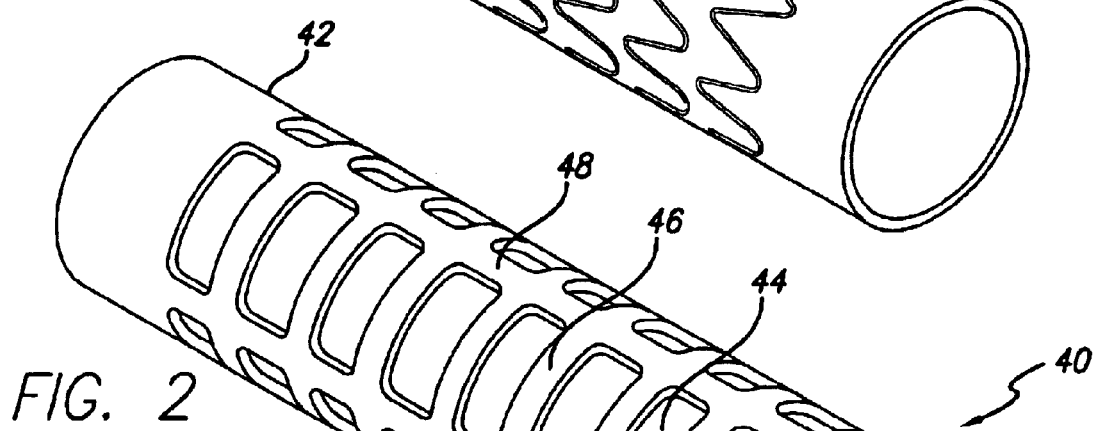
FIG. 2 is a perspective view of the "lacey" sleeve of the present invention.

FIG. 2 shows the structure of a "lacey" graft comprising a sleeve of ePTFE 40 into which apertures have been cut. This "lacey" graft 40 is placed over the ring stents 30 in the preferred embodiment. The "lacey" graft 40 is created by cutting openings 44 in a tubular ePTFE graft 42. The openings 44 were cut into the sleeve by a $CO_2$ laser, although any other cutting technology could readily be employed. The "lacey" graft 40 is slid over the ring stents 30 and the underlying tubular graft 20 to form the preferred structure 10 shown in FIG. 3. The structure 10 is then exposed to heat and pressure, such as that caused by wrapping with PTFE tape followed by heating in an oven, thereby causing the ePTFE regions of the "lacey" graft 40 to fuse or laminate to the tubular graft 20 wherever they touch each other. It should be appreciated that the circumferential sections of ePTFE 46 that are placed over the ring stents 30 can encompass many different designs. As illustrated, a sleeve 42 with openings 44 cut out is one way of accomplishing the goal of flexibility and stability. The openings 44 between the rings of ePTFE 46 can be altered to control the degree of flexibility and stability desired. In the preferred embodiment shown in FIG. 3, the "lacey" graft 40 forms a number of circumferential sections 46, which are intended to cover a portion of the circumference of each ring stent 30, leaving the ends of the zigzags uncovered. By circumferentially covering only a portion of each ring stent 30, the maximum amount of lateral flexibility is provided.

However, circumferentially covering the individual ring stents 30 without any longitudinal support would result in a structure with little longitudinal strength and stability that would be prone to "telescoping". Thus, the longitudinal sections 48 that connect the rings of ePTFE 46 are important, because the longitudinal sections 48 are completely laminated to the underlying graft 20 and act as "anti-compression" devices by resisting the shortening of the structure 10 (the double thickness of ePTFE resists telescoping of the longitudinal sections 48). The width of the circumferential sections 46 and the longitudinal sections 48 control longitudinal strength and stability versus lateral flexibility. By adjusting these parameters, grafts can be made more or less flexible with greater or lesser anti-compression strength. In the preferred embodiment, four longitudinal sections 48 are formed and the ends of the structure 10 are completely encapsulated for greater stability. Of course, a larger number of longitudinal sections 48 could be formed. Also the longitudinal sections 48 may themselves zigzag or may be helically arranged depending on how the openings 44 are cut into the sleeve 42. Each different structure will possess different properties. Similarly, the circumferential sections 46 can have different forms and may be undulating. There is nothing to preclude a covering with a more complex pattern where circumferential sections and longitudinal sections are difficult to discern or are even nonexistent.

Figure 4:
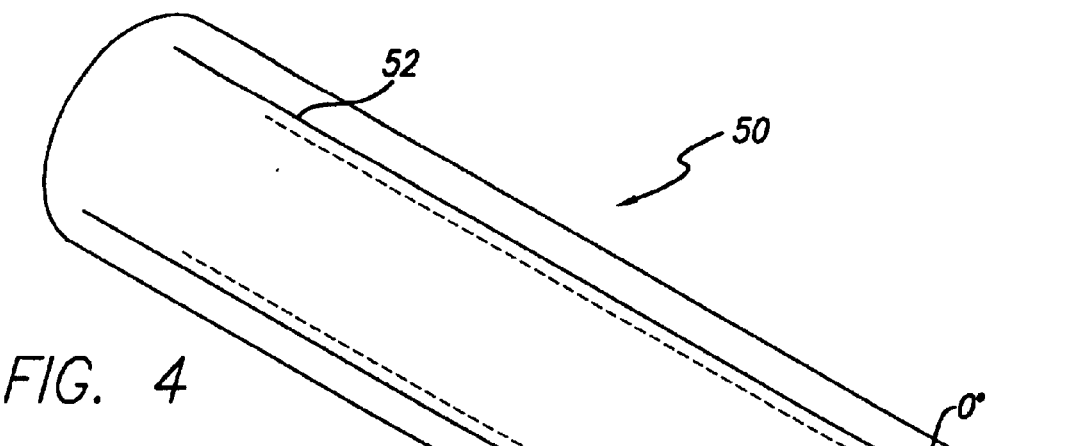
FIG. 4 is a perspective view of one configuration of the slitted sleeve of the present invention with longitudinally oriented slits.
Figure 5:
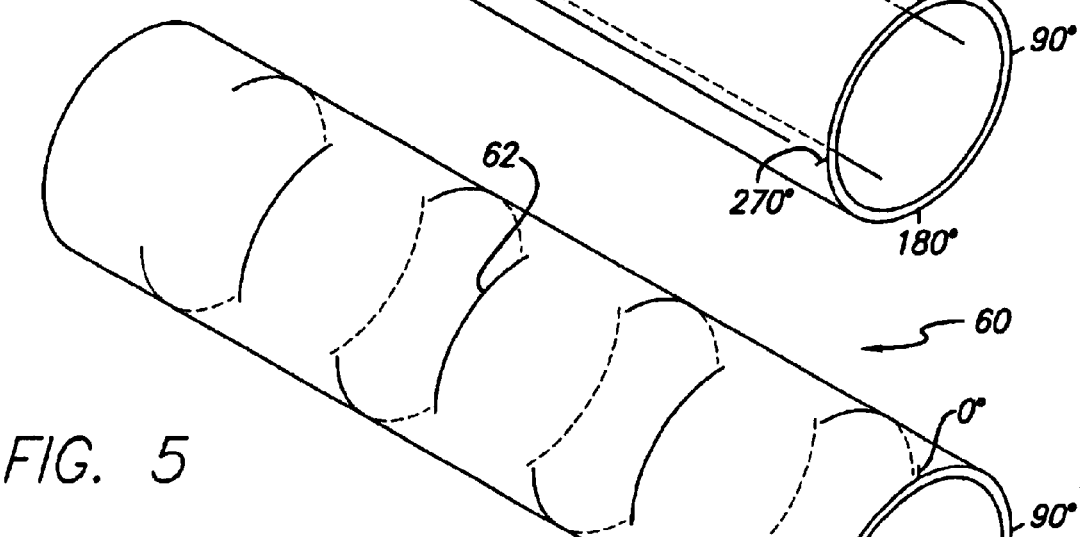
FIG. 5 is a perspective view of a second configuration of the slitted sleeve of the present invention with circumferentially oriented slits.
Figure 6:
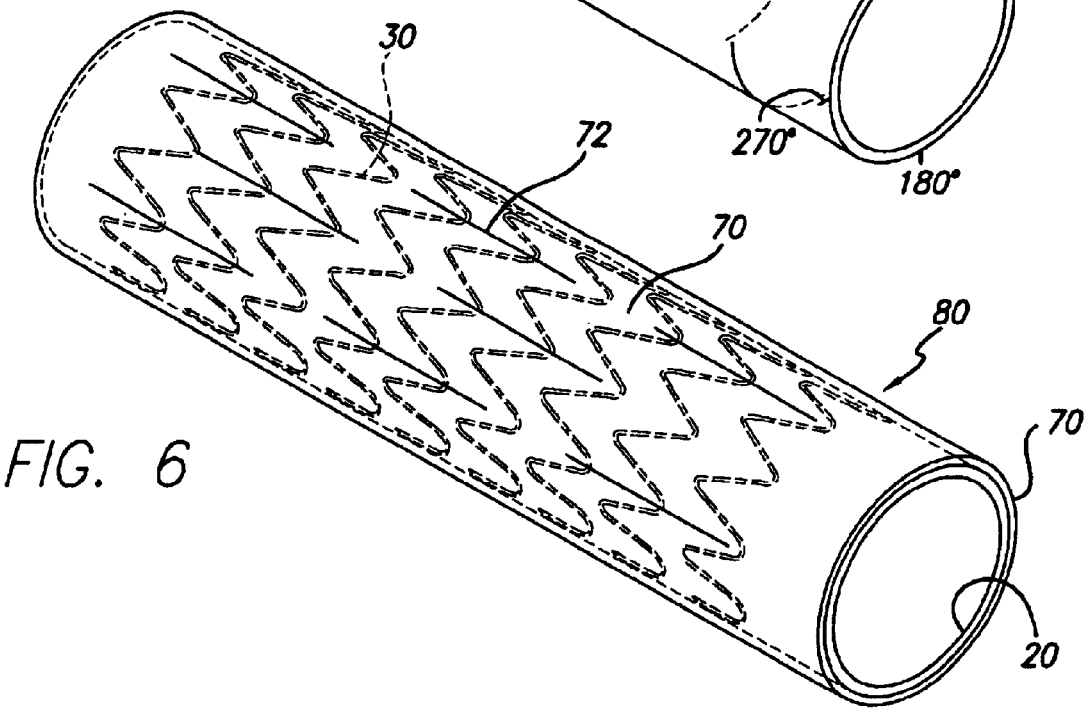
FIG. 6 is a perspective view of a third configuration of the slitted sleeve as it is placed over the structure in FIG. 1.

A second embodiment of the present invention can be seen in FIGS. 4–6. Instead of having a "lacey" graft structure, a slitted outer sleeve is used to provide partial encapsulation of the stent, the slits providing flexibility to the structure, allowing the stent to expand and retract more readily. In FIG. 4, four longitudinal slits 52 run the length of the stent, leaving 5 to 10 mm of uncut sleeve at the ends. The slits are formed at 0°, 90°, 180°, and 270°, and are oriented to pass over a peak portion of each zigzag ring stent 30 (FIG. 6). FIG. 5 shows circumferential slits 62, wherein slits are cut circumferentially around the sleeve 60 at spaced intervals, preferably to coincide with a stent ring. At each radial section, two slits are cut around the circumference at evenly spaced intervals. In a first radial section, the slits span from 0° to 90° and from 180° to 270°. Each successive radial section has a pair of slits which are offset 90° from the previous pair. Thus, a second radial section will have slits spanning from 90° to 180° and from 270° to 0°. Beside the configurations shown in FIGS. 4 and 5, a number of other slit configurations are possible, including diagonal and sinusoidal as will be appreciated by one skilled in the art. As shown in FIG. 6, a sleeve 70 is placed over the ring stents 30 and the underlying tubular graft 20 to form a new structure 80. The longitudinal slits 72, which are cut into sleeve 70, differ from the slits 52 shown in FIG. 4 in that they do not span the length of the structure 80 and are staggered around the circumference of the sleeve 70. Ideally, the slits are aligned over the peaks in the zigzag ring stents 30. Once the slits 72 are cut into the sleeve 70 using any of the known methods, the structure 80 is exposed to heat and pressure, such as that caused by wrapping with PTFE tape and heating in an oven, thereby causing the ePTFE regions of the slitted graft 70 to fuse or laminate to the tubular graft 20. The slits 72 in the slitted outer sleeve 70 can be formed by using a $CO_2$ laser, razor blade or any other suitable technique known in the art. The slits enhance the flexibility of the encapsulated structure and allow radial expansion without tearing of the ePTFE. In addition, a plurality of slits help the expanded graft to grip onto the vessel wall. This is particularly important where an encapsulated stent graft is spanning a region of damaged or weakened vessel as in an aneurysm. Further, during the healing process tissues readily grow into the slits further anchoring the graft to the vessel wall.

An advantage that cutting slits into an ePTFE sleeve offers is that it is somewhat easier to manufacture than is the "lacey" graft. Because no material is removed the sleeve is somewhat stronger than a "lacey graft". There are a multitude of configurations possible, including cutting the slits in asymmetric fashion to achieve desired results, such as using radial, longitudinal and diagonal cuts simultaneously. Moreover, a greater number of slits can be cut into a region of the structure in which greater expansion is desired.

Figure 7:
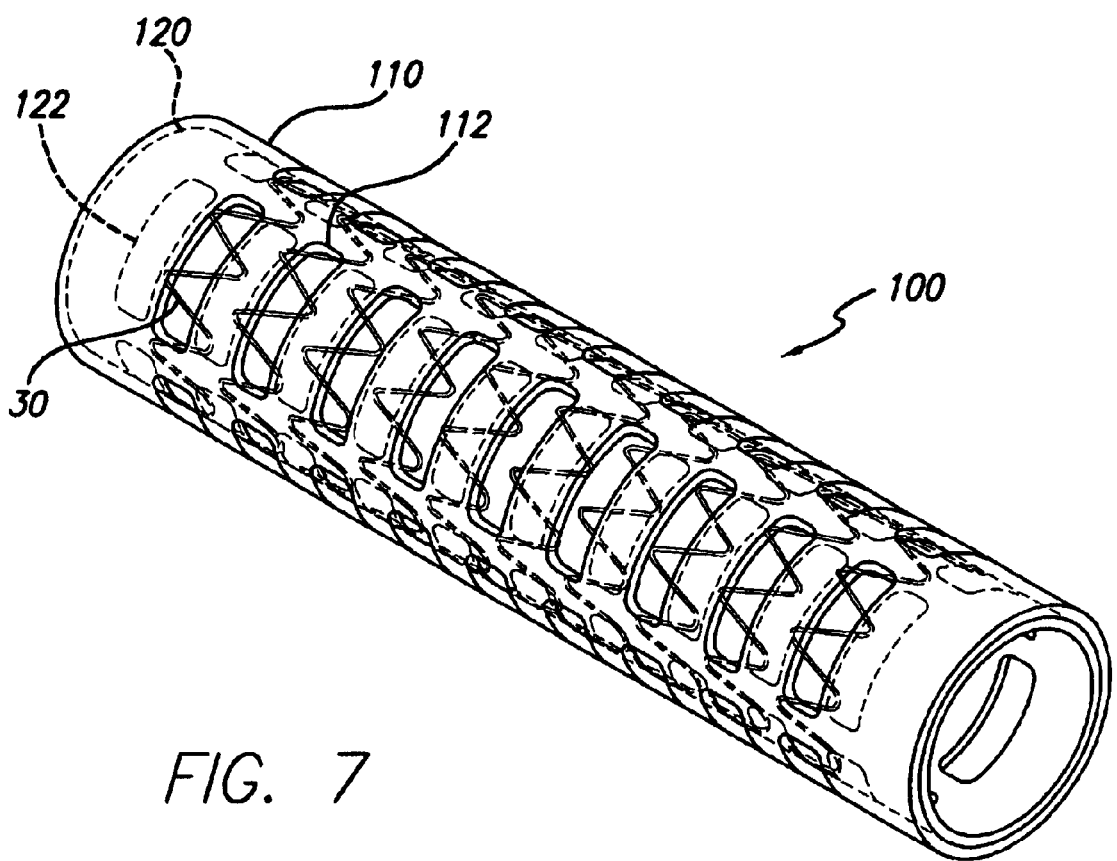
FIG. 7 is a perspective view of an alternate embodiment of the present invention.

Although the above examples are described with the "lacey" and slitted grafts being placed over a stent which is itself placed over a tubular graft, this orientation can be readily reversed. That is, the "lacey" or slitted grafts can be placed on a mandrel; a stent or stents can be then placed over the "lacey" or slitted grafts, and a tubular graft can be then placed over the stent or stents. This results in a structure wherein part or much of the luminal surface is provided by the outer graft, providing superior healing as only a single layer of ePTFE would separate body tissues from the blood. Moreover, a structure with two "lacey" or slitted grafts is possible. As shown in FIG. 7, the openings 112 in the outer graft 110 are arranged out of phase with the openings 122 in the inner graft 120. Such a configuration provides a blood tight structure wherein a majority of the final surface area of the device 100 comprises a single layer separating body tissue from the circulating blood. Also, the areas occupied by the stent(s) 30 and by overlap between the two grafts 110, 120 present a barrier to cellular infiltration. The described structure has the advantage of a smaller profile when compressed because the overall amount of PTFE is reduced. In a further embodiment, a combination of the "lacey" graft and slitted graft could be produced.

Having thus described preferred embodiments of the partial encapsulation of stents, it will be apparent by those skilled in the art how certain advantages of the present invention have been achieved. It should also be appreciated that various modifications, adaptations, and alternative embodiments thereof may be made within the scope and spirit of the present invention. For example, zigzag stent rings have been illustrated, but it should be apparent that the inventive concepts described above would be equally applicable to sinusoidal and other stent designs. Moreover, the words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result. The described embodiments are to be considered illustrative rather than restrictive. The invention is further defined by the following claims.

We claim:

1. A method for making a partially encapsulated radially expandable reinforced vascular graft, comprising:

providing a first and second tubular expanded polytetrafluoroethylene layer of material, wherein said first tubular layer is a luminal layer of said vascular graft;

creating a plurality of openings in said first and second tubular layers, each of the openings extending through a wall thereof and comprising a longitudinal component and a circumferential component, wherein the length of the longitudinal component is less than the total length of the tubular layer in which it is created, and wherein the length of the circumferential component is less than 360°;

disposing a radially expandable support layer comprising at least one stent between said first and second tubular layers;

positioning the openings over at least a portion of said support layer; and attaching said second tubular layer to said first tubular layer.

2. The method of claim 1, wherein said support layer comprises a plurality of ring stents formed in a zigzag pattern of alternating peaks and valleys, wherein the disposing step further comprises disposing the peaks and valleys of successive stents in phase.

3. The method of claim 1, wherein the attaching step further comprises laminating said second tubular layer to said first tubular layer.

4. The method of claim 1, wherein the openings comprise similarly shaped apertures, and wherein the creating step further comprises creating a ring of said apertures at a distinct point along the length of said at least one of said tubular layers.

5. The method of claim 4, wherein the creating step further comprises creating a plurality of rings of apertures along the length of at least one of said layers.

6. The method of claim 5, wherein the apertures are rectangular in shape and wherein each ring is comprised of at least three apertures.

7. The method of claim 1, further comprising the step of positioning said openings in said first tubular layer out of phase with said openings in said second tubular layer.

8. The method of claim 1, further comprising the step of encapsulating completely said support layer at each end of said vascular graft.

* * * * *